US008455436B2

(12) United States Patent
Byers et al.

(10) Patent No.: US 8,455,436 B2
(45) Date of Patent: Jun. 4, 2013

(54) COMPOSITIONS AND METHODS FOR TREATING JOINTS

(75) Inventors: Ben Byers, North Easton, MA (US); Dongling Su, Franklin, MA (US); Julia Hwang, Wayland, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 12/979,990

(22) Filed: Dec. 28, 2010

(65) Prior Publication Data
US 2012/0165257 A1 Jun. 28, 2012

(51) Int. Cl.
*A61K 38/00* (2006.01)
*A61K 38/16* (2006.01)
*A61K 38/17* (2006.01)
*A61K 38/18* (2006.01)
*A61K 38/19* (2006.01)

(52) U.S. Cl.
USPC ........... 514/8.8; 514/8.9; 514/16.7; 514/16.8; 514/17.1

(58) Field of Classification Search
None
See application file for complete search history.

(56) References Cited

U.S. PATENT DOCUMENTS

| | | | |
|---|---|---|---|
| 3,697,652 A | 10/1972 | Rovati et al. |
| 4,141,973 A | 2/1979 | Balazs |
| 4,666,897 A | 5/1987 | Golub et al. |
| 5,011,691 A | 4/1991 | Oppermann et al. |
| 5,143,724 A | 9/1992 | Leshchiner et al. |
| 5,258,371 A | 11/1993 | Golub et al. |
| 5,266,683 A | 11/1993 | Oppermann et al. |
| 5,273,056 A | 12/1993 | McLaughlin et al. |
| 5,364,845 A | 11/1994 | Henderson |
| 5,366,964 A | 11/1994 | Lindstrom et al. |
| 5,399,351 A | 3/1995 | Leshchiner et al. |
| 5,409,904 A | 4/1995 | Hecht et al. |
| 5,498,606 A | 3/1996 | Soll et al. |
| 5,510,121 A | 4/1996 | Rhee et al. |
| 5,789,395 A | 8/1998 | Amin et al. |
| 5,792,103 A | 8/1998 | Schwartz et al. |
| 5,814,621 A | 9/1998 | Kanaya et al. |
| 6,030,635 A | 2/2000 | Gertzman et al. |
| 6,051,560 A | 4/2000 | Chang et al. |
| 6,069,135 A | 5/2000 | Falk et al. |
| 6,197,326 B1 | 3/2001 | Suzuki et al. |
| 6,238,372 B1 | 5/2001 | Zinger et al. |
| 6,281,195 B1 | 8/2001 | Rueger et al. |

(Continued)

FOREIGN PATENT DOCUMENTS

DE 20 2007 011252 U1 12/2007
EP 0 517 970 A1 12/1992

(Continued)

OTHER PUBLICATIONS

ORTHOVISC detailed product information, http://www.depuy.com/sites/default/files/products/files/OrthoviscNonAvianPIFinal2010.pdf; accessed Apr. 25, 2012.*

(Continued)

*Primary Examiner* — Elizabeth C Kemmerer

(57) ABSTRACT

Methods and compositions are disclosed for an intra-articular injection for the treatment of osteoarthritis. The methods and compositions comprising combinations of hyaluronic acid and a bone morphogenetic protein, like rhGDF-5, can be useful for any synovial joint, including the knee, shoulder, hip, ankle, hands, spinal facet, or temporomandibular joint, both for the relief of pain and for slowing disease progression.

7 Claims, 8 Drawing Sheets

U.S. PATENT DOCUMENTS

| | | |
|---|---|---|
| 6,288,043 B1 | 9/2001 | Spiro et al. |
| 6,346,519 B1 | 2/2002 | Petrus |
| 6,410,044 B1 | 6/2002 | Chudzik et al. |
| 6,428,804 B1 | 8/2002 | Suzuki et al. |
| 6,437,018 B1 | 8/2002 | Gertzman et al. |
| 6,458,375 B1 | 10/2002 | Gertzman et al. |
| 6,551,801 B1 | 4/2003 | Andou et al. |
| 6,586,406 B2 | 7/2003 | Heidaran et al. |
| 6,608,043 B1 | 8/2003 | Serizawa et al. |
| 6,656,925 B2 | 12/2003 | Petrus |
| 6,677,321 B1 | 1/2004 | Levin |
| 6,699,471 B2 | 3/2004 | Radice et al. |
| RE38,522 E | 5/2004 | Gertzman et al. |
| 6,756,358 B2 | 6/2004 | Iwamoto et al. |
| 6,818,629 B2 | 11/2004 | Peterson et al. |
| 6,835,377 B2 | 12/2004 | Goldberg et al. |
| 6,906,044 B2 | 6/2005 | Hermida Ochoa |
| 6,911,212 B2 | 6/2005 | Gertzman et al. |
| 6,924,273 B2 | 8/2005 | Pierce |
| 6,924,370 B2 | 8/2005 | Chudzik et al. |
| 6,949,525 B2 | 9/2005 | Hermida |
| 6,972,321 B1 | 12/2005 | Hotten et al. |
| 6,979,679 B2 | 12/2005 | Marcum |
| 7,019,192 B2 | 3/2006 | Gertzman et al. |
| 7,025,959 B1 | 4/2006 | Hotten et al. |
| 7,026,292 B1 | 4/2006 | Lee et al. |
| 7,045,141 B2 | 5/2006 | Merboth et al. |
| 7,067,144 B2 | 6/2006 | Demopulos et al. |
| 7,070,942 B2 | 7/2006 | Heidaran et al. |
| 7,112,578 B2 | 9/2006 | Levin |
| 7,141,545 B2 | 11/2006 | Pike et al. |
| 7,189,392 B1 | 3/2007 | Kim et al. |
| RE39,587 E | 4/2007 | Gertzman et al. |
| 7,214,667 B2 | 5/2007 | Fukuda et al. |
| 7,223,744 B2 | 5/2007 | Yerxa et al. |
| 7,239,908 B1 | 7/2007 | Alexander et al. |
| 7,268,114 B2 | 9/2007 | Makishima et al. |
| 7,314,636 B2 | 1/2008 | Caseres et al. |
| 7,323,445 B2 | 1/2008 | Zhang et al. |
| 7,425,573 B2 | 9/2008 | Pelletier et al. |
| 7,485,629 B2 | 2/2009 | Marcum |
| 7,582,311 B1 | 9/2009 | Cleland et al. |
| 7,592,009 B2 | 9/2009 | Hubbell et al. |
| 7,608,580 B2 | 10/2009 | Kim et al. |
| 7,651,682 B2 | 1/2010 | Devore et al. |
| 7,651,703 B2 | 1/2010 | Cleland et al. |
| 7,763,116 B2 | 7/2010 | Carter et al. |
| 7,931,030 B2 | 4/2011 | Bailleul |
| 2003/0031697 A1 | 2/2003 | Chudzik et al. |
| 2003/0086899 A1 | 5/2003 | Jafari |
| 2003/0181371 A1 | 9/2003 | Hunter et al. |
| 2003/0223983 A1* | 12/2003 | Sofia et al. ............... 424/94.63 |
| 2004/0038929 A1 | 2/2004 | Fukuda et al. |
| 2004/0082540 A1 | 4/2004 | Hermida Ochoa |
| 2004/0147466 A1 | 7/2004 | Barman et al. |
| 2004/0214793 A1 | 10/2004 | Hermida Ochoa |
| 2004/0241248 A1 | 12/2004 | Margalit et al. |
| 2005/0025765 A1 | 2/2005 | DiMauro et al. |
| 2005/0100538 A1 | 5/2005 | Mohamed et al. |
| 2005/0112186 A1 | 5/2005 | Devore et al. |
| 2005/0232981 A1 | 10/2005 | Ben-Sasson |
| 2005/0250737 A1 | 11/2005 | Hughes et al. |
| 2006/0040894 A1* | 2/2006 | Hunter et al. ................ 514/54 |
| 2006/0073207 A1 | 4/2006 | Masters et al. |
| 2006/0122147 A1 | 6/2006 | Wohlrab |
| 2006/0122150 A1 | 6/2006 | Argentieri et al. |
| 2006/0210552 A1 | 9/2006 | Demopulos et al. |
| 2007/0053987 A1 | 3/2007 | Bayer et al. |
| 2007/0149441 A1 | 6/2007 | Aeschlimann et al. |
| 2007/0172517 A1 | 7/2007 | Ben-Sasson et al. |
| 2007/0190149 A1 | 8/2007 | Zahos |
| 2007/0203095 A1 | 8/2007 | Sadozai et al. |
| 2007/0275055 A1 | 11/2007 | Ben-Sasson et al. |
| 2007/0286881 A1 | 12/2007 | Burkinshsw |
| 2008/0118523 A1 | 5/2008 | Hubbell et al. |
| 2008/0145404 A1 | 6/2008 | Hill et al. |
| 2008/0147065 A1 | 6/2008 | McKay et al. |
| 2008/0147077 A1 | 6/2008 | Garigapati et al. |
| 2008/0167235 A1 | 7/2008 | Zhang et al. |
| 2009/0017091 A1 | 1/2009 | Daniloff |
| 2009/0017093 A1 | 1/2009 | Springer et al. |
| 2009/0035315 A1 | 2/2009 | Christgau et al. |
| 2009/0087503 A1 | 4/2009 | Henderson et al. |
| 2009/0099089 A1 | 4/2009 | Zhang et al. |
| 2009/0104148 A1 | 4/2009 | Jay et al. |
| 2009/0118348 A1 | 5/2009 | Miyamoto et al. |
| 2009/0123547 A1 | 5/2009 | Hill et al. |
| 2009/0124552 A1 | 5/2009 | Hill et al. |
| 2009/0136576 A1 | 5/2009 | Calvosa et al. |
| 2009/0162351 A1 | 6/2009 | Brown et al. |
| 2009/0162376 A1 | 6/2009 | Brown et al. |
| 2009/0181007 A1 | 7/2009 | Gennero et al. |
| 2009/0181058 A1 | 7/2009 | Li et al. |
| 2009/0202430 A1 | 8/2009 | Hoemann et al. |
| 2009/0202642 A1 | 8/2009 | Huang et al. |
| 2009/0291112 A1 | 11/2009 | Truncale et al. |
| 2010/0217231 A1 | 8/2010 | Ilan et al. |
| 2013/0005681 A1 | 1/2013 | Su et al. |

FOREIGN PATENT DOCUMENTS

| | | |
|---|---|---|
| EP | 2 033 689 A1 | 3/2009 |
| EP | 2251359 A1 | 11/2010 |
| FR | 2866571 A1 | 8/2005 |
| JP | 11-302197 A | 11/1999 |
| JP | 2003-160464 A | 6/2003 |
| JP | 2004-359629 A | 12/2004 |
| JP | 3-748970 B2 | 2/2006 |
| KR | 2008-0024426 A | 3/2008 |
| WO | 94/28889 A1 | 12/1994 |
| WO | 97/24374 A1 | 7/1997 |
| WO | 97/28788 A1 | 8/1997 |
| WO | 98/22114 A1 | 5/1998 |
| WO | 99/40926 A1 | 8/1999 |
| WO | 03/034993 A2 | 5/2003 |
| WO | 03/043660 A2 | 5/2003 |
| WO | 2004/032943 A1 | 4/2004 |
| WO | 2005/110439 A2 | 11/2005 |
| WO | 2008/098019 A2 | 8/2008 |
| WO | 2009/005790 A2 | 1/2009 |
| WO | 2009/024670 A2 | 2/2009 |
| WO | 2009132228 A1 | 10/2009 |
| WO | 2011/086458 A1 | 7/2011 |

OTHER PUBLICATIONS

Celeste et al. PNAS 87:9843-47 (1990).

Cheng et al. "Osteogenic activity of the fourteen types of human bone morphogenetic proteins" J. Bone Joint Surg. Am. 85A: 1544-52 (2003).

Honda, et al, Journal of Bioscience and Bioengineering 89(6), 582-589 (2000).

Lyons et al. PNAS 86:4554-58 (1989).

Massague Annu. Rev. Cell Biol. 6:957 (1990).

Ozkaynak et al. EMBO J. 9:2085-93 (1990).

Ruppert, et al Eur J Biochem 237, 295-302 (1996).

Sampath, et al. J. Biol. Chem. 265:13198 (1990).

Wharton, et al. PNAS 88:9214-18 (1991).

Remington's Pharmaceutical Sciences, 15th ed. Easton: Mack Publishing Co.: 1405-1412, 1461-1487, 1975.

The National Formulary XIV., 14th ed. Washington: American Pharmaceutical Association, 1975 Table of Contents only.

Extended European Search Report issued Mar. 20, 2012 for Application No. 11195499.6 (5 Pages).

Gilman et al., eds., Goodman and Gilman's: The Pharmacological Basis for Therapeutics. Table of contents. 4 pages. Seventh Edition, 1985, Macmillan Publishers, London.

[No author listed] Greenfield Pharmacy, 1999, pp. 1-2.

[No author listed] United Sugars Corporation, 2010, p. 1.

European Partial Search Report for Application No. 12/746,143, issued Aug. 14, 2012. (9 pages).

Mankin et al., J Clin Invest 1971;50:1712-9.

Benaroudj et al., Biol Chem. 2001;276:24261-7.

Yoshizane et al., Nutrition Res. 2000;20:1485-91.

Minutoli, Shock, vol. 27(1), 91-96 (2007).
Chen, J Exp Biol, 207, 3125-3129 (2004).
Birch, Advances in Carbohydrate Chem, vol. 18, 201-225 (1963).
Hoelzle, Applied Env Microbiol, vol. 56, 3,213-3,215 (1990).
[No Author Listed] Euflexxae® Product information sheet. May, 2011, 2 pages.

[No. Author Listed] Orthovisc®. Manufactured by Anika Therapeutics, Inc. of Bedford, MA. Retrieved Mar. 30, 2011 from <http://www.orthovisc.com/orthvisc>, 2 pages.
[No Author Listed] Shiseido. Sodium Hyaluronate. Medical Grade. 1993, 4 pages.

* cited by examiner

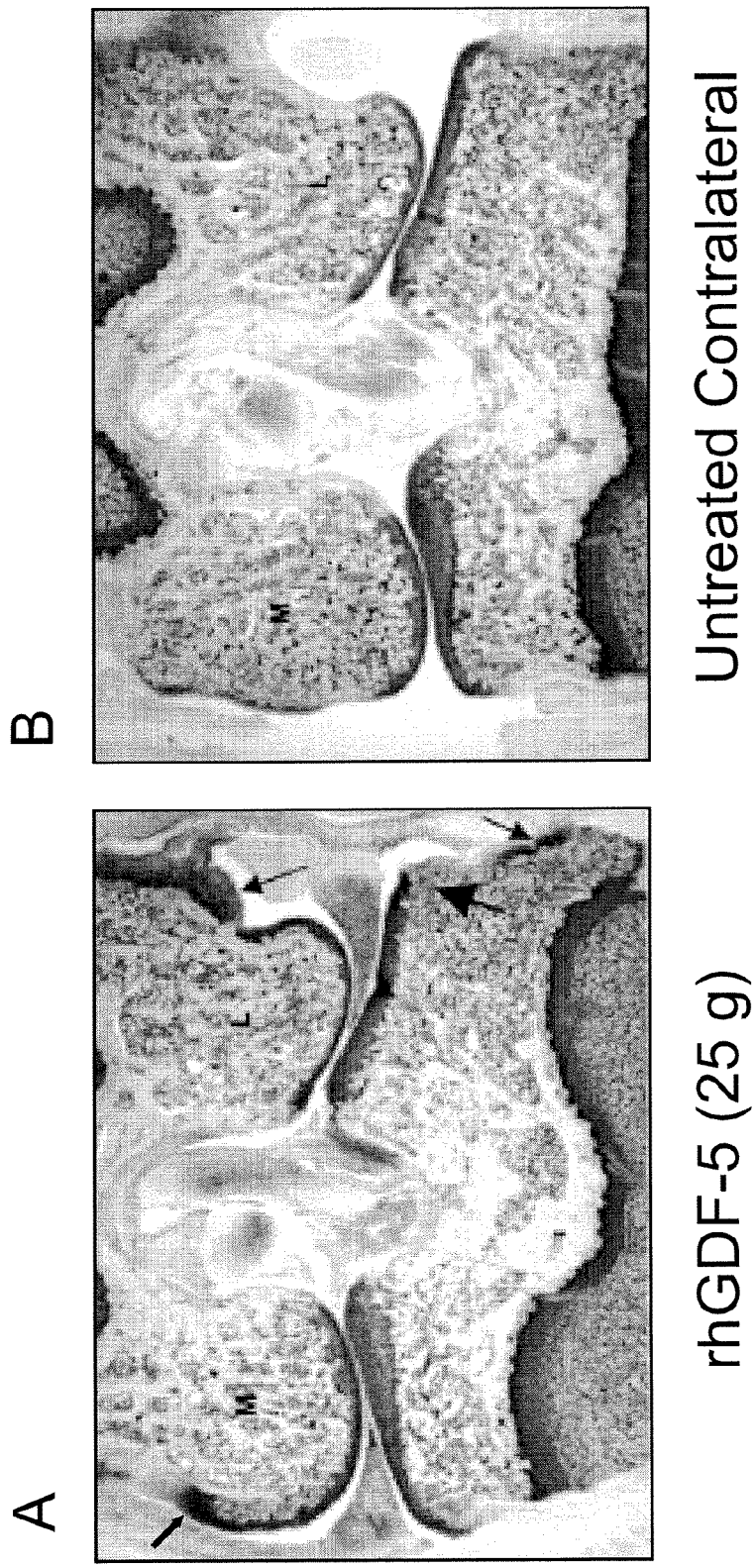

```
SEQUENCE LISTING

<160> NUMBER OF SEQ ID NOS: 5

<210> SEQ ID NO 1
<211> LENGTH: 662
<212> TYPE: PRT
<213> ORGANISM: Homo sapiens

<400> SEQUENCE: 1

Met Lys Lys Phe Ser Arg Met Pro Lys Ser Glu Gly Gly Ser Gly Gly
1               5                   10                  15

Gly Ala Ala Gly Gly Ala Gly Gly Ala Gly Ala Gly Ala Gly Cys
            20                  25                  30

Gly Ser Gly Gly Ser Ser Val Gly Val Arg Val Phe Ala Val Gly Arg
        35                  40                  45

His Gln Val Thr Leu Glu Glu Ser Leu Ala Glu Gly Gly Phe Ser Thr
    50                  55                  60

Val Phe Leu Val Arg Thr His Gly Gly Ile Arg Cys Ala Leu Lys Arg
65                  70                  75                  80

Met Tyr Val Asn Asn Met Pro Asp Leu Asn Val Cys Lys Arg Glu Ile
                85                  90                  95

Thr Ile Met Lys Glu Leu Ser Gly His Lys Asn Ile Val Gly Tyr Leu
            100                 105                 110

Asp Cys Ala Val Asn Ser Ile Ser Asp Asn Val Trp Glu Val Leu Ile
        115                 120                 125

Leu Met Glu Tyr Cys Arg Ala Gly Gln Val Val Asn Gln Met Asn Lys
    130                 135                 140

Lys Leu Gln Thr Gly Phe Thr Glu Pro Glu Val Leu Gln Ile Phe Cys
145                 150                 155                 160

Asp Thr Cys Glu Ala Val Ala Arg Leu His Gln Cys Lys Thr Pro Ile
                165                 170                 175

Ile His Arg Asp Leu Lys Val Glu Asn Ile Leu Leu Asn Asp Gly Gly
            180                 185                 190

Asn Tyr Val Leu Cys Asp Phe Gly Ser Ala Thr Asn Lys Phe Leu Asn
        195                 200                 205

Pro Gln Lys Asp Gly Val Asn Val Val Glu Glu Ile Lys Lys Tyr
```

```
                    210                 215                 220
Thr Thr Leu Ser Tyr Arg Ala Pro Glu Met Ile Asn Leu Tyr Gly Gly
225                 230                 235                 240

Lys Pro Ile Thr Thr Lys Ala Asp Ile Trp Ala Leu Gly Cys Leu Leu
                    245                 250                 255

Tyr Lys Leu Cys Phe Phe Thr Leu Pro Phe Gly Glu Ser Gln Val Ala
                260                 265                 270

Ile Cys Asp Gly Asn Phe Thr Ile Pro Asp Asn Ser Arg Tyr Ser Arg
            275                 280                 285

Asn Ile His Cys Leu Ile Arg Phe Met Leu Glu Pro Asp Pro Glu His
        290                 295                 300

Arg Pro Asp Ile Phe Gln Val Ser Tyr Phe Ala Phe Lys Phe Ala Lys
305                 310                 315                 320

Lys Asp Cys Pro Val Ser Asn Ile Asn Asn Ser Ser Ile Pro Ser Ala
                    325                 330                 335

Leu Pro Glu Pro Met Ala Ala Ser Glu Ala Ala Arg Lys Ser Gln
                340                 345                 350

Ile Lys Ala Arg Ile Thr Asp Thr Ile Gly Pro Thr Glu Thr Ser Ile
            355                 360                 365

Ala Pro Arg Gln Arg Pro Lys Ala Asn Ser Ala Thr Thr Ala Thr Pro
370                 375                 380

Ser Val Leu Thr Ile Gln Ser Ser Ala Thr Pro Val Lys Val Leu Ala
385                 390                 395                 400

Pro Gly Glu Phe Ser Asn His Arg Pro Lys Gly Ala Leu Arg Pro Gly
                    405                 410                 415

Asn Gly Pro Glu Ile Leu Leu Gly Gln Gly Pro Pro Gln Gln Pro Pro
                420                 425                 430

Gln Gln His Arg Val Leu Gln Gln Leu Gln Gln Gly Asp Trp Arg Leu
            435                 440                 445

Gln Gln Leu His Leu Gln His Arg His Pro His Gln Gln Gln Gln Gln
        450                 455                 460

Gln Gln Gln Gln Gln Gln Gln Gln Gln Gln Gln Gln Arg Gln Gln
465                 470                 475                 480

Gln Gln Gln Gln Gln Gln His His His His His His His Leu Leu
                    485                 490                 495

Gln Asp Ala Tyr Met Gln Gln Tyr Gln His Ala Thr Gln Gln Gln Gln
                500                 505                 510

Met Leu Gln Gln Gln Phe Leu Met His Ser Val Tyr Gln Pro Gln Pro
            515                 520                 525

Ser Ala Ser Gln Tyr Pro Thr Met Met Pro Gln Tyr Gln Gln Ala Phe
        530                 535                 540

Phe Gln Gln Gln Met Leu Ala Gln His Gln Pro Ser Gln Gln Gln Ala
545                 550                 555                 560

Ser Pro Glu Tyr Leu Thr Ser Pro Gln Glu Phe Ser Pro Ala Leu Val
                    565                 570                 575

Ser Tyr Thr Ser Ser Leu Pro Ala Gln Val Gly Thr Ile Met Asp Ser
                580                 585                 590

Ser Tyr Ser Ala Asn Arg Ser Val Ala Asp Lys Glu Ala Ile Ala Asn
            595                 600                 605

Phe Thr Asn Gln Lys Asn Ile Ser Asn Pro Pro Asp Met Ser Gly Trp
        610                 615                 620

Asn Pro Phe Gly Glu Asp Asn Phe Ser Lys Leu Thr Glu Glu Glu Leu
625                 630                 635                 640
```

-continued

```
Leu Asp Arg Glu Phe Asp Leu Leu Arg Ser Ser Lys Gly His Leu Lys
            645                 650                 655

Ala Tyr Phe Ala Ser Gln
            660

<210> SEQ ID NO 2
<211> LENGTH: 431
<212> TYPE: PRT
<213> ORGANISM: Homo sapiens

<400> SEQUENCE: 2

Met His Val Arg Ser Leu Arg Ala Ala Pro His Ser Phe Val Ala
  1               5                  10                  15

Leu Trp Ala Pro Leu Phe Leu Leu Arg Ser Ala Leu Ala Asp Phe Ser
               20                  25                  30

Leu Asp Asn Glu Val His Ser Ser Phe Ile His Arg Arg Leu Arg Ser
           35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
   65                  70                  75                  80

Met Phe Met Leu Asp Leu Tyr Asn Ala Met Ala Val Glu Glu Gly Gly
               85                  90                  95

Gly Pro Gly Gly Gln Gly Phe Ser Tyr Pro Tyr Lys Ala Val Phe Ser
           100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
   130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
               165                 170                 175

Tyr Lys Asp Tyr Ile Arg Glu Arg Phe Asp Asn Glu Thr Phe Arg Ile
           180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
   210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
               245                 250                 255

Ile Asn Pro Lys Leu Ala Gly Leu Ile Gly Arg His Gly Pro Gln Asn
           260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
   290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
               325                 330                 335

Val Ser Phe Arg Asp Leu Gly Trp Gln Asp Trp Ile Ile Ala Pro Glu
           340                 345                 350
```

```
Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 501
<212> TYPE: PRT
<213> ORGANISM: Homo sapiens

<400> SEQUENCE: 3

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
290                 295                 300
```

-continued

```
Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Arg Gln Val
            325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 4
<211> LENGTH: 271
<212> TYPE: PRT
<213> ORGANISM: Homo sapiens

<400> SEQUENCE: 4

Met Asp Thr Pro Arg Val Leu Leu Ser Ala Val Phe Leu Ile Ser Phe
1               5                   10                  15

Leu Trp Asp Leu Pro Gly Phe Gln Gln Ala Ser Ile Ser Ser Ser Ser
            20                  25                  30

Ser Ser Ala Glu Leu Gly Ser Thr Lys Gly Met Arg Ser Arg Lys Glu
        35                  40                  45

Gly Lys Met Gln Arg Ala Pro Arg Asp Ser Asp Ala Gly Arg Glu Gly
    50                  55                  60

Gln Glu Pro Gln Pro Arg Pro Gln Asp Glu Pro Arg Ala Gln Gln Pro
65                  70                  75                  80

Arg Ala Gln Glu Pro Pro Gly Arg Gly Pro Arg Val Val Pro His Glu
                85                  90                  95

Tyr Met Leu Ser Ile Tyr Arg Thr Tyr Ser Ile Ala Glu Lys Leu Gly
            100                 105                 110

Ile Asn Ala Ser Phe Phe Gln Ser Ser Lys Ser Ala Asn Thr Ile Thr
        115                 120                 125

Ser Phe Val Asp Arg Gly Leu Asp Asp Leu Ser His Thr Pro Leu Arg
130                 135                 140

Arg Gln Lys Tyr Leu Phe Asp Val Ser Met Leu Ser Asp Lys Glu Glu
145                 150                 155                 160

Leu Val Gly Ala Glu Leu Arg Leu Phe Arg Gln Ala Pro Ser Ala Pro
                165                 170                 175
```

```
Trp Gly Pro Pro Ala Gly Pro Leu His Val Gln Leu Phe Pro Cys Leu
            180                 185                 190

Ser Pro Leu Leu Leu Asp Ala Arg Thr Leu Asp Pro Gln Gly Ala Pro
        195                 200                 205

Pro Ala Gly Trp Glu Val Phe Asp Val Trp Gln Gly Leu Arg His Gln
    210                 215                 220

Pro Trp Lys Gln Leu Cys Leu Glu Leu Arg Ala Ala Pro Gly Pro Ala
225                 230                 235                 240

Glu Ser Gly Leu Arg Pro Gly Ala Ala Ser Pro Gly Ala Gly Pro
                245                 250                 255

Ala Gly Gly Ile His Gln Ile Pro Ala Ala Cys Pro Pro Asn
            260                 265                 270

<210> SEQ ID NO 5
<211> LENGTH: 453
<212> TYPE: PRT
<213> ORGANISM: Homo sapiens

<400> SEQUENCE: 5

Met Asp Leu Ser Ala Ala Ala Leu Cys Leu Trp Leu Leu Ser Ala
1               5                   10                  15

Cys Arg Pro Arg Asp Gly Leu Glu Ala Ala Val Leu Arg Ala Ala
                20                  25                  30

Gly Ala Gly Pro Val Arg Ser Pro Gly Gly Gly Gly Gly Gly Gly
            35                  40                  45

Gly Gly Gly Gly Arg Thr Leu Ala Gln Ala Gly Ala Ala Ala
        50                  55                  60

Val Pro Ala Ala Val Pro Arg Ala Arg Ala Arg Ala Ala
65                  70                  75                  80

Gly Ser Gly Phe Arg Asn Gly Ser Val Val Pro His His Phe Met Met
                85                  90                  95

Ser Leu Tyr Arg Ser Leu Ala Gly Arg Ala Pro Ala Gly Ala Ala Ala
                100                 105                 110

Val Ser Ala Ser Gly His Gly Arg Ala Asp Thr Ile Thr Gly Phe Thr
            115                 120                 125

Asp Gln Ala Thr Gln Asp Glu Ser Ala Ala Glu Thr Gly Gln Ser Phe
    130                 135                 140

Leu Phe Asp Val Ser Ser Leu Asn Asp Ala Asp Glu Val Val Gly Ala
145                 150                 155                 160

Glu Leu Arg Val Leu Arg Arg Gly Ser Pro Glu Ser Gly Pro Gly Ser
                165                 170                 175

Trp Thr Ser Pro Pro Leu Leu Leu Ser Thr Cys Pro Gly Ala Ala
                180                 185                 190

Arg Ala Pro Arg Leu Leu Tyr Ser Arg Ala Ala Glu Pro Leu Val Gly
    195                 200                 205

Gln Arg Trp Glu Ala Phe Asp Val Ala Asp Ala Met Arg Arg His Arg
    210                 215                 220

Arg Glu Pro Arg Pro Arg Ala Phe Cys Leu Leu Leu Arg Ala Val
225                 230                 235                 240

Ala Gly Pro Val Pro Ser Pro Leu Ala Leu Arg Arg Leu Gly Phe Gly
                245                 250                 255

Trp Pro Gly Gly Gly Ser Ala Ala Glu Glu Arg Ala Val Leu Val
            260                 265                 270

Val Ser Arg Thr Gln Arg Lys Glu Ser Leu Phe Arg Glu Ile Arg
        275                 280                 285
```

```
Ala Gln Ala Arg Ala Leu Gly Ala Ala Leu Ala Ser Glu Pro Leu Pro
    290             295             300

Asp Pro Gly Thr Gly Thr Ala Ser Pro Arg Ala Val Ile Gly Gly Arg
305             310             315                         320

Arg Arg Arg Arg Thr Ala Leu Ala Gly Thr Arg Thr Ala Gln Gly Ser
            325             330             335

Gly Gly Gly Ala Gly Arg Gly His Gly Arg Arg Gly Arg Ser Arg Cys
            340             345             350

Ser Arg Lys Pro Leu His Val Asp Phe Lys Glu Leu Gly Trp Asp Asp
        355             360             365

Trp Ile Ile Ala Pro Leu Asp Tyr Glu Ala Tyr His Cys Glu Gly Leu
        370             375             380

Cys Asp Phe Pro Leu Arg Ser His Leu Glu Pro Thr Asn His Ala Ile
385             390             395                         400

Ile Gln Thr Leu Leu Asn Ser Met Ala Pro Asp Ala Ala Pro Ala Ser
            405             410             415

Cys Cys Val Pro Ala Arg Leu Ser Pro Ile Ser Ile Leu Tyr Ile Asp
            420             425             430

Ala Ala Asn Asn Val Val Tyr Lys Gln Tyr Glu Asp Met Val Val Glu
        435             440             445

Ala Cys Gly Cys Arg
    450
```

COMPOSITIONS AND METHODS FOR TREATING JOINTS

FIELD OF THE INVENTION

The present invention relates generally to compositions and methods for treating joints.

BACKGROUND OF THE INVENTION

Osteoarthritis ("OA"), the most common form of arthritis, is a type of arthritis that is characterized by degenerative (gradual deterioration of joint) or abnormal changes in bone, cartilage, and synovium of the joints. OA is often characterized by a progressive wearing down of opposing joint surfaces accompanied at times by inflammation resulting in pain, swelling, and stiffness for the patient. OA can occur in one or more joints following trauma to the joint, following an infection of the joint, or simply as a result of aging. Furthermore, there is emerging evidence that abnormal anatomy may contribute to early development of OA.

Treatment of OA generally involves a combination of exercise or physical therapy, lifestyle modification, and analgesics. Acetaminophen is typically the first line treatment for OA. For mild to moderate symptoms, effectiveness is similar to non-steroidal anti-inflammatory drugs ("NSAIDs"), such as ibuprofen. For more severe symptoms NSAIDs may be more effective. However, while more effective, NSAIDs in severe cases are associated with greater side effects such as gastrointestinal bleeding and renal complications. Another class of NSAIDs, COX-2 selective inhibitors (such as Celecoxib), are equally effective to NSAIDs but no safer in terms of side effects. There are several NSAIDs available for topical use, including diclofenac. Typically, they have less systemic side-effects than oral administration and at least some therapeutic effect. While opioid analgesics, such as morphine and fentanyl, improve pain this benefit is outweighed by frequent adverse events and thus they are not routinely used. Intra-articular steroid injections are also used in the treatment of OA, and they are very effective at providing pain relief. However, the durability of the pain relief is limited to 4-6 weeks and there are adverse effects that may include collateral cartilage damage. If pain becomes debilitating, joint replacement surgery may be used to improve mobility and quality of life. There is no proven treatment to slow or reverse the disease.

For patients who do not get adequate pain relief from simple pain relievers, like acetaminophen or from exercise and physical therapy, intra-articular injections of hyaluronic acid (HA) provide another treatment option to address symptomatic pain and delay the need for a total joint replacement surgery. It is known that the concentration of native HA is deficient in individuals suffering from OA and therefore joint injections of exogenous HA is believed to replenish these molecules and restore the viscoelastic properties of synovial fluid. It is this property that is responsible for lubricating and cushioning the joints. There is also evidence that HA has biological activity through binding to cell surface receptors and may have a role in mitigating inflammation. Independent of the mechanism of action, pain relief is observed for about six months following a treatment course. A treatment course for HA products on the US market can range from single injection product to others that require 3 to 5 weekly injections to attain this durability of pain relief.

There remains a need for improved methods and compositions for treating OA joints, and to address the pain and structural degeneration associated with OA.

SUMMARY OF THE INVENTION

In one aspect, a method for treating a joint condition is disclosed. The method includes combining a solution of hyaluronic acid (HA) with a bone morphogenetic protein (BMP) to form a mixture in which the BMP is precipitated and dispersed in the solution of HA and the mixture has a pH of at least about 3, preferably in the range of about 3 to 8, and more preferably in the range of about 5-7.5. The method further includes injecting the mixture into a subject to treat the OA joint condition, such that the BMP is capable of becoming solubilized and biologically active within the subject after injection.

In one embodiment, the BMP can be a growth and differentiation factor protein, such as growth and differentiation factor 5 (GDF-5), growth and differentiation factor 6 (GDF-6) and growth and differentiation factor 7 (GDF-7). In another embodiment, the BMP can be BMP2 or BMP7.

In another embodiment, BMP is present in the mixture at a concentration in the range of about 5 µg/ml to 2000 µg/ml, and more preferably in the range of about 5 µg/ml to 500 µg/ml. Furthermore, the BMP can be in a liquid state or a solid/lyophilized state which then can be combined with HA. When in a liquid form, the BMP can be solubilized in an acid solution, e.g., hydrochloric acid, with a pH of less than about 4.

In yet another embodiment, the HA can have a molecular weight of at least about 500 kilodaltons (kDa), and more preferably the HA has a molecular weight of at least about 1 million daltons. Additionally, compositions include HA at a concentration in the range of about 5mg/ml to 60 mg/ml, and more preferably between 7 and 30 mg/ml. The HA can also be present in a liquid state or a solid/lyophilized state prior to combining with the BMP. When in a liquid form, the HA can be solubilized in water, saline or buffered solution, or any other diluents known in the art. The HA solution can also have a pH in the range of about 5 to 9 prior to combination. After combining the BMP with the HA solution, the mixture can have a pH in the range of about 3 to 8.

In another aspect, a composition for treating a joint condition is disclosed. The composition can be in the form of an injectable formulation that includes a precipitate of a bone morphogenetic protein (BMP) dispersed within a solution of hyaluronic acid (HA). The injectable formulation can have a pH of at least about 3. Moreover, the BMP is present in the injectable formulation in a precipitated form that is capable of becoming solubilized and biologically active after injection into an organism.

In one more aspect, a method for forming a composition for treating a joint disorder is disclosed. The method can include combining a solution of hyaluronic acid (HA) and a bone morphogenetic protein (BMP) and allowing the combination to form a mixture containing a precipitate of the BMP that is dispersed within the HA solution. The BMP in the resulting composition is in its precipitated form and capable of becoming solubilized and biologically active following delivery to an organism.

In yet another aspect, a kit is disclosed. The kit can include a first component being a solution of hyaluronic acid (HA) having a pH in the range of about 3 to 8, a second component including an amount of a bone morphogenetic protein (BMP) that is in precipitate form and capable of becoming solubilized and biologically active following delivery to an organism, and a syringe for injecting a mixture of the first component and the second component. Moreover, the syringe can have a first chamber containing the first component, a second container containing the second component and a plunger configured to inject the second component into the first chamber to mix the first and second components.

BRIEF DESCRIPTION OF THE DRAWINGS

The appended drawings have been included herein so that the above-recited features, advantages and objects will become clear and can be understood in detail. These drawings form a part of the specification. It is to be noted, however, that the appended drawings illustrate exemplary embodiments and should not be considered to limit the scope.

FIGS. 8A and 8B are photomicrographs illustrating in vivo and intra-articular bioactivity of rhGDF-5 in the HA formulations.

DETAILED DESCRIPTION OF THE INVENTION

Figure 1:
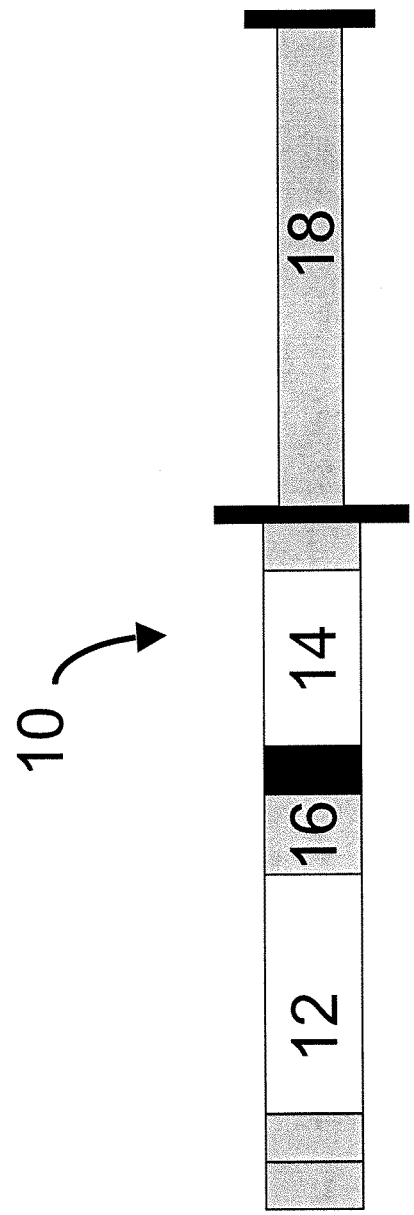
FIG. 1 is a perspective view of one embodiment of a mixing and delivery system for use with the compositions and methods of the present invention.

In general, the present invention provides compositions and methods for treating joint conditions, such as pain associated with osteoarthritis. The compositions and methods utilize hyaluronic acid ("HA") in combination with one or more Bone Morphogenetic Proteins ("BMP"). In one embodiment the BMP is present as a precipitate that is dispersed within a solution of HA. The composition can be formulated as an injectable formulation that has a pH of at least about 3, and the pH can be in the range of about 3 to 8, more preferably 4 to 7.5, even more preferably 5 to 7.5. The composition can be used in a method of treating a joint condition by administering the composition to a subject, such as by injection into the body of the subject (e.g., by injection into a joint) as discussed below. Various BMPs are suitable for use in the composition, as described below. Exemplary BMPs include a growth and differentiation factor (GDF), such as GDF-5, GDF-6, and GDF-7, and bone morphogenetic proteins (BMPs), such as BMP2 and BMP7.

Hyaluronic Acid

Hyaluronic acid, HA, can have various formulations and can be provided at various concentrations and molecular weights. The terms "hyaluronic acid," "hyaluronan," and "HA" are used interchangeably herein to refer to hyaluronic acids or salts of hyaluronic acid, such as the sodium, potassium, magnesium, and calcium salts, among others. These terms are also intended to include not only elemental hyaluronic acid, but hyaluronic acid with other trace elements or in various compositions with other elements. The terms "hyaluronic acid," "hyaluronan," and "HA" encompass chemical or polymeric or cross-linked derivatives of HA. Examples of chemical modifications which may be made to HA include any reaction of an agent with the four reactive groups of HA, namely the acetamido, carboxyl, hydroxyl, and the reducing end. The HA used in the present application is intended to include natural formulations, synthetic formulations, or combinations thereof. The HA can be provided in liquid or solid formulations, and the HA can be in pure liquid form or in a solvent at various concentrations.

HA is a glycosaminoglycan (GAG), and in particular HA is an unbranched polysaccharide made up of alternating glucuronic acid and N-acetyl glucosamine units. It is a viscoelastic material that is also found in the extracellular matrix of cartilage bound to collagen. In particular, HA is an important building component of aggregated proteoglycans which impart resilient characteristics of articular cartilage. HA not only helps keep the cartilage that cushions joints strong and flexible, but it also helps increase supplies of joint-lubricating synovial fluid. HA abnormalities are a common thread in connective tissue disorders. HA can thus be used, to prevent, treat, or aid in the surgical repair of connective tissue disorders.

HA can be used in the compositions and methods of the present invention at various molecular weights. Since HA is a polymeric molecule, the HA component can exhibit a range of molecular weights, and almost any average of modal molecular weight formulation of HA can be used in the compositions and methods of the present invention, including Low Molecular Weight ("LWM") Hyaluronan (about 500 to 700 kilodaltons (kDa), Medium Molecular Weight ("MMW") Hyaluronan (700-1000 kDa), and High Molecular Weight ("HMW") Hyaluronan (1.0-4.0 million daltons (MDa)). In certain exemplary embodiments, the HA has a molecular weight of at least about 500 kDa, and more preferably the HA is a High Molecular Weight ("HWM") HA having a molecular weight of at least about 1 MDa. The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 kDa or more, or any range derivable therein. It is expected that chemically modified HA's could have very different molecular weights than described above. A crosslinked HA can likewise have much higher molecular weight than noted above. Regardless, these materials are also applicable in this invention.

Solvents that can be used to solubilize HA include, but are not limited to, water, saline or other salt solutions, buffer solutions such as phosphate buffered saline, histidine, lactate, succinate, glycine, and glutamate, dextrose, glycerol, as well as combinations thereof.

A person skilled in the art will appreciate that the compositions and methods of the present invention can include various other joint treatment or excipients, including, for example, amino acids, proteins, saccharides, di-saccharides, poly-saccharides, nucleic acids, buffers, surfactants and mixtures thereof. Steroids, anti-inflammatory agents, non-steroidal anti-inflammatory agents, analgesics, cells, stabilizers, antibiotics, antimicrobial agents, anti-inflammatory agents, growth factors, growth factor fragments, small-molecule wound healing stimulants, hormones, cytokines, peptides, antibodies, enzymes, isolated cells, platelets, immunosuppressants, nucleic acids, analgesics, cell types, viruses, virus particles, and combinations thereof.

The concentration of HA present in the mixture can also vary, but in an exemplary embodiment HA is provided at a pharmaceutically effective amount. In an exemplary embodiment, the HA has a concentration of at least about 5 mg/ml, and more preferably at least about 7 mg/ml, and more preferably at least about 10 mg/ml, and more preferably at least about 15 mg/ml, and in some embodiments the concentration can be at least about 20 mg/ml. Suitable concentrations of HA include about 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59mg/l, 60 mg/ml or more or any range derivable therein.

In one embodiment, the first component comprises an HA having a high molecular weight (1 to 4 MDa) having a concentration in the range of about 7-40 mg/ml. One such product is Orthovisc® manufactured by Anika Therapeutics, Inc. of Bedford, Mass. Orthovisc® is a sterile, non-pyrogenic, clear, viscoelastic solution of hyaluronan. Orthovisc® consists of high molecular weight (1.0-2.9 MDa), ultra-pure natural hyaluronan dissolved in physiological saline and having a nominal concentration of 15 mg/ml. Orthovisc® is isolated through bacterial fermentation. One skilled in the art will recognize that there are companies such as Shiseido and Lifecore who can produce high molecular weight HA through a bacterial fermentation process. Another example of an HA product available in the United States with these characteristics is Euflexxa®.

While HA alone can be effective to treat joint conditions, HA combined with additional agents should provide additional benefits. In particular, Bone Morphogenetic Proteins (BMPs) can help bone and cartilage regeneration by effecting chondrogenesis. This invention addresses the difficulty in administering HA in combination with BMPs since BMPs are not soluble at neutral pHs. BMPs are soluble in acidic solutions, however, it is not desirable to have an HA formulation at a sufficiently low pH to solubilize the BMP. This is because HA is not stable at low pH and will degrade with time. However, a product that combines BMP and HA and is maintained at a neutral/slightly acidic pH can ensure that the BMP can remain stable during and after the precipitation process, and demonstrate biological activity following precipitation and subsequent injection into a patient. Having a near neutral pH formulation is also desirable from the perspective of the patient because there could be discomfort to the patient who receives injections of such acidic solutions. Thus, it has been discovered that the use of solid BMPs dispersed in solution combined with HA provide substantial benefits over HA alone. In particular, although the BMPs precipitate when combined with HA at or near neutral pH, the BMPs are able to resolubilize and become biologically active after injection into a patient's body. It is believed that the BMPs are not biologically active (or they have reduced biological activity) in their solid, precipitated form in HA, however upon resolubilization after injection into a patient's body, the BMPs regain their biological activity and/or become more biologically active than in their solid, precipitated form.

Bone Morphogenetic Proteins

The term "bone morphogenetic proteins," as used herein embraces the class of proteins typified by representatives of the TGF-f3 family subclass of true tissue morphogens. The BMPs that are useful can include, but are not limited to, growth and differentiation factors (in both monomeric and dimeric forms) (such as GDF-5, GDF-6 and GDF-7) and bone morphogenetic proteins (such as BMP2 and BMP7).

All members of this family share common structural features, including a carboxy terminal active domain, and are approximately 97-106 amino acids in mature length. They are translated as precursor proteins consisting of a prodomain, which is released proteolytically by members of the subtilisin-like proprotein convertase family, which is important to activate signaling that is conferred through the mature domain. All members share a highly conserved pattern of cysteine residues that create three intramolecular disulfide bonds and one intermolecular disulfide bond. The active form can be either a disulfide-bonded homodimer of a single family member or a heterodimer of two different members. (See Massague Annu Rev. Cell Biol. 6:957 (1990); Sampath, et al. J. Biol. Chem. 265:13198 (1990); Ozkaynak et al. EMBO J. 9:2085-93 (1990); Wharton, et al. PNAS 88:9214-18 (1991); Celeste et al. PNAS 87:9843-47 (1990); Lyons et al. PNAS 86:4554-58 (1989), U.S. Pat. No. 5,011,691, and U.S. Pat. No. 5,266,683).

Osteogenic BMPs were initially identified by their ability to induce ectopic endochondral bone formation. (See Cheng et al. "Osteogenic activity of the fourteen types of human bone morphogenetic proteins" J. Bone Joint Surg. Am. 85A: 1544-52 (2003)). In particular, BMP2 (SEQ ID NO:1) and BMP7 (SEQ ID NO:2) play an important role in the development of bone and cartilage. BMP2 has been shown to stimulate the production of bone. BMP7 also plays a key role in the transformation of mesenchymal cells into bone and cartilage.

Growth/differentiation factors (GDF-1 to GDF-15) are initially synthesized as larger precursor proteins which subsequently undergo proteolytic cleavage at a cluster of basic residues approximately 110-140 amino acids from the C-terminus, thus releasing the C-terminal mature protein parts from the N-terminal prodomain. The mature polypeptides are structurally related and contain a conserved bioactive domain comprising six or seven canonical cysteine residues which is responsible for the characteristic three-dimensional "cysteine-knot" motif of these proteins. The mature proteins contain seven conserved cysteine residues that are assembled into active secreted homodimers. GDF dimers are disulfide-linked with the exception of GDF-3 and GDF-9. It will be appreciated by one skilled in the art that the term "GDF" is used interchangeably with "rhGDF."

GDF-5 (SEQ ID NO:3) is a morphogen which has been shown to promote cell proliferation, differentiation and/or tissue formation in several tissues. The protein is also known as morphogenetic protein MP52, bone morphogenetic protein BMP-14, and cartilage-derived morphogenetic protein-1 (CDMP-1). GDF-5 is closely related to GDF-6 (SEQ ID NO:4) and GDF-7 (SEQ ID NO:5), all of which can be used according to the present invention in combination with HA. These three proteins form a distinct subgroup of the TGF-β superfamily, thus displaying comparable biological properties and an extraordinary high degree of amino acid sequence identity. It has repeatedly been demonstrated that members of the GDF-5/-6/-7 subgroup are primarily important inducers and regulators of bone and cartilage as well as tendon/ligament.

Native GDF-5 proteins are homodimeric molecules and act mainly through interaction with specific receptor complexes which are composed of type I and type II serine/threonine receptor kinases. The receptor kinases subsequently activate SMAD proteins, which then propagate the signals into the nucleus to regulate target gene expression.

Biological molecules (biomolecules), such as BMPs, have three-dimensional structure or conformation, and rely on this structure for their biological activity and properties. Exposing these biomolecules to various environments such as variations in pH, temperature, solvents, osmolality, etc., can irreversibly change or denature the conformational state of the biomolecule, rendering it biologically inactive.

The chemistry and the three dimensional structure of each BMP family member impacts the solubility of the protein in an aqueous environment. BMP-2 is readily soluble at concentrations greater than 1 mg/ml when the pH is below 6, and above pH 6 the solubility can be increased by the addition of 1 M NaCl, 30% isopropanol, or 0.1 mM heparin (Ruppert, et al Eur J Biochem 237, 295-302 (1996)). The solubility of BMP-7/OP-1 is also limited at neutral pH. The solubility of GDF-5 is much more limited than that of BMP-2 of -7, and GDF-5 is nearly insoluble in physiological pH ranges and buffers. GDF-5 is only soluble in water at pH 2 to 4 (Honda, et al, Journal of Bioscience and Bioengineering 89(6), 582-589 (2000)). GDF-5 is soluble at an alkaline pH of about 9.5 to 12.0, however proteins degrade quickly under these conditions and thus acidic conditions have typically been used for preparation of GDF-5 protein. Solubility of these proteins are not only controlled by pH but are also affected by the salt concentrations or other active ingredients in the solution. For example, if there is an active ingredient in solution that the protein will bind to, it can cause insolubility of the protein.

Growth factors, such as BMPs, have been combined with other components. Due to the fact that solubility of most BMP's is limited at neutral pH, as noted above, BMP's are likely to precipitate out of solution in response to combination with neutral solutions, such as soluble HA. Many efforts have been made to prevent the precipitation and/or increase the maintenance of a bioactive BMP when combined with such components. However, no combinations have been previously disclosed for the utilization of a solid form of BMP, either precipitate or lyophilized, in a HA solution. The present compositions and methods combine a solid or lyophilized formulation of BMP, such as rhGDF-5, with a liquid formulation of HA. In another embodiment, compositions and methods are disclosed that form a mixture by combining a solution of BMP with a solution of HA, wherein the BMP forms a precipitate upon such a combination. These two components, solubilized HA and precipitated BMP, combined together form the mixture that is subsequently administered to a patient. As noted above, the three dimensional conformation is crucial for the activity of proteins including growth factors. The act of aggregating or precipitating such a molecule in solution can disturb the three dimensional structure leading to loss of activity of the protein. Therefore, those skilled in the art have typically taken precautions to prevent change in conformation or structure of proteins because these changes can be irreversible.

One skilled in the art will appreciate that the term "precipitation," as used herein, refers to the formation of an insoluble protein in the solution. In contrast to known examples of drugs that are delivered as a suspension (due to the fact that the carrier, e.g., a mineral, ceramic, metal, or polymeric, is insoluble rather than the active protein) an aspect of the invention disclosed herein is the active precipitation of the protein immediately prior to delivery of the mixture to a patient.

When in a liquid formulation, the BMP can be provided in water, saline, an acid solution (e.g., hydrochloric acid, acetic acid, benzoic acid), another acidic solvent, or another solvent suitable for solubilization of BMP.

The concentration of BMP present in the mixture can also vary, but in an exemplary embodiment BMP is provided at a pharmaceutically effective amount. In an exemplary embodiment, the BMP has a concentration of at least about 0.1 µg/ml, and more preferably at least about 5 µg/ml, and more preferably at least about 50 µg/ml, and more preferably at least about 200 µg/ml, and in some embodiments the concentration can be at least about 500 µg/ml. Suitable concentrations of BMP include about 5 µg/ml, 6 µg/ml, 7 µg/ml, 8 µg/ml, 9 µg/ml, 10 µg/ml, 11 µg/mg, 12 µg/ml, 13 µg/ml, 14 µg/ml, 15 µg/ml, 16 µg/ml, 17 µg/ml, 18 µ/ml, 19 µg/ml, 20 µg/ml, 21 µg/ml, 22 µg/ml, 23 µg/ml, 24 µg/ml, 25 µg/ml, 26 µmg/ml, 27 µg/ml, 28 µg/ml, 29 µg/ml, 30 µg/ml, 31 µg/ml, 32 µg/ml, 33 µg/ml, 34 µg/ml, 35 µg/ml, 37 µg/ml, 38 µg/ml, 39 µg/ml, 40 µg/ml, 41 µg/ml, 42 µmg/ml, 43 µg/ml, 44 µg/ml, 45 µg/ml, 46 µg/ml, 47 µg/ml, 48 µg/ml, 49 µg/ml, 50 µg/ml, 60 µg/ml, 70 µg/ml, 80 µg/ml, 90 µg/ml, 100 µg/ml, 150 µg/ml, 200 µg/ml, 250 µg/ml, 300 µg/ml, 350 µg/ml, 400 µg/ml, 450 µg/ml, 500 µg/ml, 550 µg/ml, 600 µg/ml, 650 µg/ml, 700 µg/ml, 750 µg/ml, 800 µg/ml, 850 µg/ml, 900 µg/ml, 950 µg/ml, 1000 µg/ml, 1500 µg/ml, or 2000 µg/ml or more or any range derivable therein. A person skilled in the art can determine a suitable concentration of BMP from methods known in the pharmaceutical arts, and that determination will govern the nature and the concentration of BMP in the composition.

Lyophilization

Any one or more of the components present in the compositions and methods of the present invention can be lyophilized using various techniques known in the art. Lyophilization is a dehydration process that is typically used to preserve a perishable material, and it works by freezing the material and then reducing the surrounding pressure and adding enough heat to allow the frozen water in the material to sublime directly from the solid phase to the gas phase. Standard lyophilization techniques known in the art can be used to lyophilize any one or more of the components. In an exemplary embodiment, at a minimum the one or more BMPs are lyophilized.

Prior to lyophilization, various solvents can be used to form an aqueous mixture containing the component(s) to be lyophilized. In an exemplary embodiment, the aqueous mixture is prepared by combining water with one or more of the components. The component(s) can be present within the mixture at various amounts, for example in the range of about 0.05 mg/mL to 10 mg/ml rhGDF-5.[there is no preferred]. In an exemplary embodiment, the composition is filter sterilized, such as with a 0.2 µm filter, prior to lyophilization.

In one embodiment, the component(s) can be lyophilized using the following cycle:

Freezing: from ambient temperature to 5° C. in 15 minutes
Hold at 5° C. for 100 minutes
Down to −45° C. in 50 minutes
Hold at −45° C. for 180 minutes
Primary Drying: set pressure at 50 mTorr
Shelf Up to −15° C. in 175 minutes
Hold at −15° C. for 2300 minutes
Secondary Drying: set pressure at 75 mTorr
Shelf Up to 25° C. in 200 minutes
Hold for 900 minutes
Cycle end: backfill with nitrogen to ~730 Torr
Capping and crimping Variations to the temperatures, times and settings can be made in accordance to practices used by a person of skilled in the art. Variations may include, but are not limited to, cycling temperatures for the freezing cycle, drying temperatures and end cycles. Variations may also include differences in holding times for the freezing, drying and capping/crimping cycles. Variations may also include differences in set pressures for the drying cycles and capping/crimping cycles. In addition, the number of drying cycles may be increased or decreased depending the machine used or component(s) to be lyophilized.

The addition of a buffering agent can provide for improved solubility and stability of the protein in lyophilized formulations. Biocompatible buffering agents known in the art can be used, such as glycine; sodium, potassium, or calcium salts of acetate; sodium, potassium, or calcium salts of citrate; sodium, potassium, or calcium salts of lactate; sodium or potassium salts of phosphate, including mono-basic phosphate, di-basic phosphate, tri-basic phosphate and mixtures thereof. The buffering agents can additionally have sugar added to the composition to function as a bulking agent. The pH preferably can be controlled within about 2.0 to about 5.0 pH units, and more preferably within about 2.5 to about 3.5 pH units.

Formulations

In an exemplary embodiment, the components are configured to be combined intraoperatively, i.e., immediately before or during an operation. The components, when combined, can form a resulting composition or mixture having each component present in the composition at various amounts. The amount of each component in the composition can vary, but in an exemplary embodiment, The mixing ratio between HA and BMP can have a weight ratio of HA to BMP in the range of about 1:0.001 to about 1:0.3, and more preferably at a ratio in the range of about 1:0.005 to about 5:1. In other embodiments, a range of ratios, or more or any range derivable therein, between about 1:0.005 to about 5:1 of HA to BMP can be useful. Alternatively, compositions can include about 1% to about 75% or more by weight of each of the individual components, such as HA and BMP, in the total composition, alternatively about 2.5%, 5%, 10%, 20%, 30%, 40%, 50%, 60%, 70% or more by weight of HA and BMP in the total composition. In an exemplary embodiment, the amount of HA present in the disclosed compositions is about 1-4% by weight of the total composition, and the amount of BMP present in the disclosed compositions is no more than 2% by weight of the total composition.

Solvents that can be used to solubilize one or more of the components include, for example, water, acidic solvents, hydrochloric acid, acetic acid, benzoic acid, phosphate buffered saline, dextrose, glycerol, ethanol and the like, as well as combinations thereof. Solvents that can be used to solubilize HA can include, but are not limited to, water, saline or other salt solutions, buffer solutions such as phosphate buffered saline, histidine, lactate, succinate, glycine and glutamate, dextrose, glycerol,and other suitable solvents, as well as combinations thereof. Solvents that can be used to solubilize the BMP can include water, saline, hydrochloric acid, acetic acid, benzoic acid, acidic solvent, and other solvents suitable for solubilization of BMPs. The compositions can also include other components, such as dispersion media, coatings, antibacterial and antifungal agents, isotonic and absorption delaying agents, and the like that are physiologically compatible. Isotonic agents include, for example, sugars, polyalcohols such as mannitol, sorbitol, or sodium chloride in the composition. The composition can also include minor amounts of auxiliary substances such as wetting or emulsifying agents, preservatives or buffers, which enhance the shelf life or effectiveness of the composition.

The components and/or the resulting composition can be sterilized prior to use using various techniques known in the art. Sterile injectable mixtures can be prepared by incorporating the active compound(s) in a therapeutically effective or beneficial amount in an appropriate solvent with one or a combination of ingredients, as required, followed by filtered sterilization. Generally, dispersions are prepared by incorporating a compound(s), such as HA or BMP, into a sterile vehicle which contains a basic dispersion medium and any required other ingredients. In the case of sterile powders for the preparation of sterile injectable mixtures, some methods can include preparation of vacuum dried and freeze-dried components which yield a powder of the composition plus any additional desired ingredients from a previously sterile-filtered mixture thereof.

The compositions can be incorporated into pharmaceutical compositions suitable for administration to a subject. Typically, the pharmaceutical composition comprises HA and at least one BMP and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, hydrochloric acid, acetic acid, benzoic acid, acidic solvent, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the composition.

The compositions can be in a variety of forms. These include, for example, liquid, semi-solid and solid dosage forms, such as liquid solutions (e.g., injectable and infusible solutions), dispersions or suspensions, tablets, pills, and powders. The preferred form depends on the intended mode of administration and therapeutic application. Typical preferred compositions are in the form of injectable or infusible solutions, such as compositions similar to those used for in vivo injection. The preferred mode of administration is parenteral (e.g., intra-articular, subcutaneous, intraperitoneal, intramuscular). In one embodiment, the composition can be administered by infusion or injection directly into the target area, such as a joint. In another embodiment, the composition can be administered by intramuscular or subcutaneous injection.

Sterile injectable solutions can be prepared by incorporating the active compound in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof Delivery Systems The methods and compositions encompass kits for treating articular disorders, such as joints. The kits can comprise of a first component, such as HA, and a second component, such as at least one BMP. Both components can be housed in a single or separate chambers of a syringe for injecting a mixture of the first and second components. In one embodiment, the BMP can be lyophilized GDF-5. In another embodiment, the BMP can be lyophilized GDF-6 or GDF-7. In another embodiment, the second component can comprise more than one lyophilized BMP, selected from BMP2, BMP7, GDF-5, GDF-6 and GDF-7. In another exemplary embodiment, a kit is provided having HA and BMP components. The HA component can comprise about 2 ml of Orthovisc®, which contains about 30 mg of hyaluronan, 18 mg of sodium chloride, and up to about 2.0 mL of water for injection. The HA has a molecular weight in the range of about 1.0 to 4 MDa. The BMP component can comprise about 0.005 to 3 mg of solid BMP, supplied by, for example, and lyophilized using the protocol discussed above. The BMP component need not be lyophilized and alternatively can be in a solution, as noted above, before combination with the HA component.

Compounds can be stored separately to increase shelf-life. The individual compounds can be lyophilized or in solid form in one syringe/cartridge with diluent or a second compound in a second syringe/cartridge. In one embodiment, one of the compounds is in lyophilized form or in solid form and the second compound is a solution capable of combining with the lyophilized/solid compound. An example can be at least one lyophilized or solid BMP can be stored in a first chamber and a solubilized HA can be stored in a second chamber. In another embodiment, both compounds can be lyophilized or in solid form and housed in a single or separate chambers of a syringe/cartridge. In another embodiment, compounds can be lyophilized directly in the syringe or cartridge.

Pre-filled dual-chamber syringes and/or cartridges can also be utilized with the components and compositions. Pre-filled dual-chamber syringes enable the sequential administration of two separate compositions with a single syringe push, thereby replacing two syringes with one. The benefits of a single delivery capability include increasing the speed and ease of drug administration; reducing risk of infection by reducing the number of connections; lowering the risk of drug administration or sequence errors, and quicker delivery of compositions requiring combination prior to administration. The dual-chamber syringe can accommodate lyophilized, powder or liquid formulations in the front chamber combined with diluents, saline or buffer in the rear chamber.

Prefilled syringes can contain the exact deliverable dose of desired compounds and diluents. The prefilled syringes can contain volumes from about 0.1 ml, 0.2 ml, 0.3 ml, 0.4 ml, 0.5 ml, 0.6 ml, 0.7 ml, 0.8 ml, 0.9 ml, 1.0 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, 10 ml or more or any derivative therein.

The dual syringe and/or cartridge can be side-by-side chambers with separate syringe plungers that mix into a single chamber or linear chambers with one plunger. The dual chamber syringe and/or cartridges can also have a stopper or connector in the middle to serve as a barrier between the two chambers. The stopper or connector can be removed to allow mixing or combining of the compounds in the two chambers.

FIG. 1 illustrates one embodiment of a mixing and delivery system that is in the form of a dual chamber syringe 10. As shown, the dual chamber syringe 10 generally includes a housing having proximal and distal chambers 14, 12 separated by a valve 16. A plunger 18 is slidably disposed within the proximal chamber 14 and is configured to inject fluid present within the proximal chamber 14 into the distal chamber 12 to thereby mix the components. In one embodiment, the first component, e.g., liquid HA, can be present in the proximal chamber 14 and the second component, e.g., one or more BMPs, can be present in the distal chamber 12. The plunger 18 can be advanced through the proximal chamber 14 to inject the first component, e.g., liquid HA, into the distal chamber 12 containing the second component, e.g., one or more BMPs. In another embodiment, the proximal chamber 14 can contain a solvent, such as water or saline, and the distal chamber 12 can contain all of the components in solid form. For example, the distal chamber 12 can contain lyophilized or solid HA and one or more BMPs. The plunger 18 can be advanced through the proximal chamber 14 to inject the solvent into the distal chamber 12, thereby solubilizing the components in the distal chamber 12. Once all components are combined in the distal chamber 12, the mixture can be delivered to tissue, for example by attaching a needle to the distal end of the dual chamber syringe.

Figure 2:
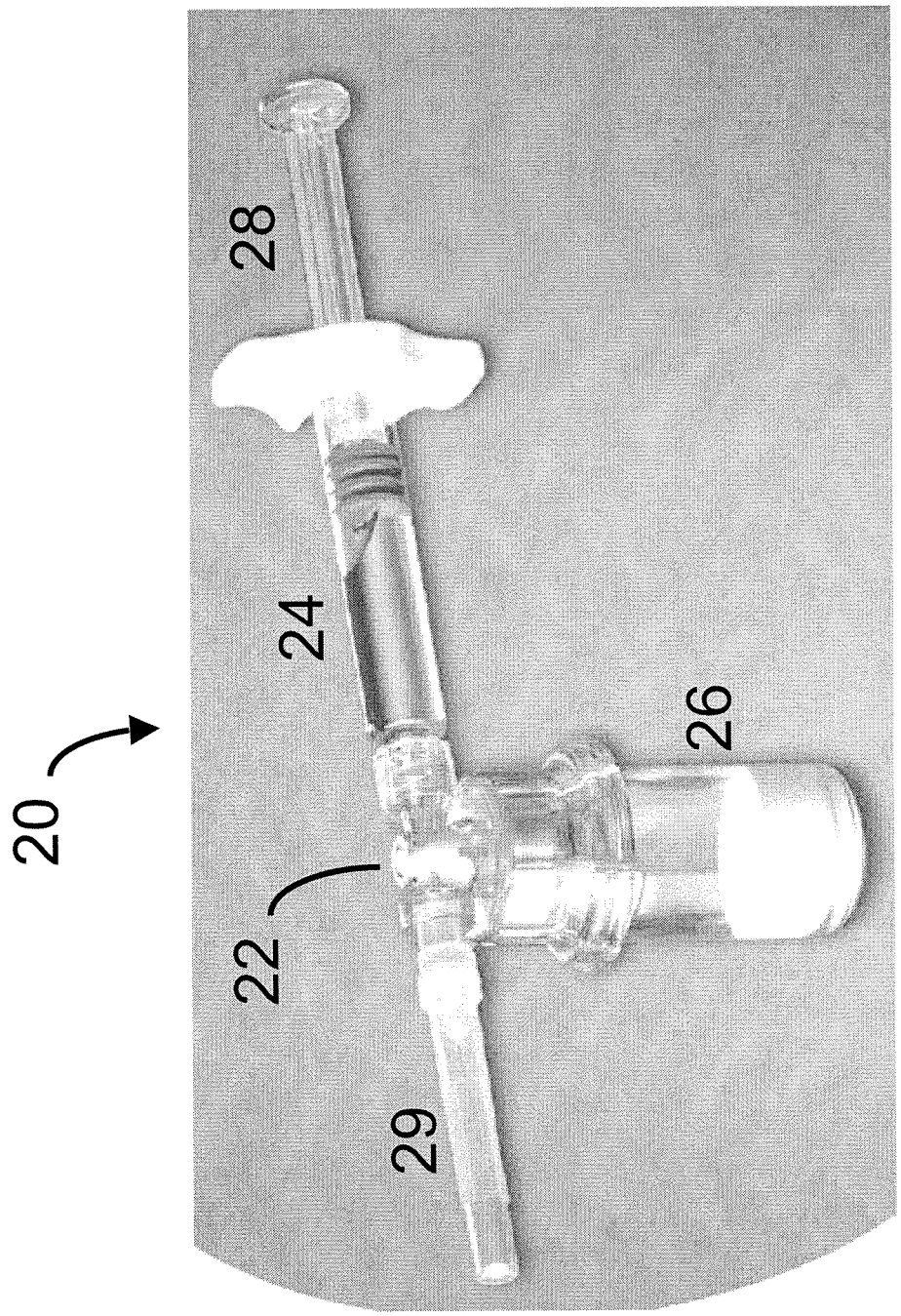
FIG. 2 is a perspective view of another embodiment of a mixing and delivery system for use with the compositions and methods of the present invention.

FIG. 2 illustrates another embodiment of a mixing and delivery system 20, which is sold commercially under the trade name MixJect®. In this embodiment, the system includes a fluid control assembly 22 that is coupled between a syringe 24 and a vial 26. The syringe 24 defines a first chamber 24a (not labeled in figure) which can contain a liquid, such as liquid HA or a solvent, and the vial defines a second chamber 26a (not labeled on figure) which can contain a solid, such as one or more BMPs. Deployment of the plunger 28 through the syringe 24 will inject the liquid through the control system and into the vial 26, where the solid will be solubilized by the liquid. Once the components are fully solubilized, the vial 26 can be inverted and the plunger 28 can be retracted to draw the mixture back into the chamber 24a in the syringe 24. The vial 26 can then be removed from the system, and the mixture can be injected from the syringe through a needle 29 and into tissue.

A person skilled in the art will appreciate that any dual chamber systems known in the art can be used, and that the chambers can be side-by-side chambers with separate syringe plungers that mix into a single chamber or linear chambers with a single plunger.

Treatments

The method and compositions can be administered, for in vivo applications, parenterally by injection or by gradual perfusion over time. Administration may be intraarticular, intravenous, intraperitoneal, intramuscular, subcutaneous, intracavity, or transdermal. For in vitro studies the agents may be added or dissolved in an appropriate biologically acceptable buffer and added to a cell or tissue.

The HA and inactive BMP can be co-administered or simultaneously administered in the same formulation or in two different formulations that are combined via the same route. The HA and BMP components can be combined just prior to administration of the HA and inactive BMP.

The combination can occur within seconds, minutes, hours, days or weeks prior to the administration of the composition.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

Frequently used "carriers" or "auxiliaries" include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co.: 1405-1412, 1461-1487, 1975 and The National Formulary XIV., 14th ed. Washington: American Pharmaceutical Association, 1975 the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

Examples of symptoms or diseases, for which the composition and methods disclosed herein can be useful, encompass treating articular disorders, such as arthritis caused by infections, injuries, allergies, metabolic disorders, etc., rheumatoids such as chronic rheumatoid arthritis, and systemic lupus erythematosus; articular disorders accompanied by gout, arthropathy such as osteoarthritis, internal derangement, hydrarthrosis, stiff neck, lumbago, etc. Varying the effects depending on the use of the composition or the types of diseases to be treated, the agent can exert desired prophylactic and alleviative effects, or even therapeutic effects on swelling, pain, inflammation, and destroying of articulations without seriously affecting living bodies. The composition for treating articular disorder can be used to prevent the onset of articulation disorders, as well as to improve, alleviate, and cure the symptoms after their onsets.

The methods of treatment can include directly injecting the compositions into the target area, such as a joint. Injections can be performed as often as daily, weekly, several times a week, bi monthly, several times a month, monthly, or as often as needed as to provide relief of symptoms. For intra-articular use, from about 1 to about 40 mg/ml of HA and one or more BMPs per joint, depending on the size of the joint and severity of the condition, can be injected. The frequency of subsequent injections into a given joint are spaced to the time of recurrence of symptoms in the joint. Illustratively, dosage levels in humans of the composition can be: knee, about 0.001 to about 40 mg/ml per joint injection; shoulder, about 0.001 to about 40 mg/ml of HA and one or more BMPs per joint injection; metacorpal or proximal intraphalangeal, about 0.001/ml to about 40 mg/ml of HA and one or more BMPs per joint injection; and elbow, about 1 to about 300 mg per joint injection.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy. The pharmaceutical compositions can be prepared and administered in dose units. Under certain circumstances, however, higher or lower dose units may be appropriate. The administration of the dose unit can be carried out both by single administration of the composition or administration can be performed in several smaller dose units and also by multiple administrations of subdivided doses at specific intervals.

In one embodiment, the medical condition is osteoarthritis (OA) and the composition is administered in a joint space, such as, for example, a knee, shoulder, temporo-mandibular and carpo-metacarpal joints, elbow, hip, wrist, ankle, and lumbar zygapophysial (facet) joints in the spine. The viscosupplementation may be accomplished via a single injection or multiple intraarticular injections administered over a period of weeks into the knee or other afflicted joints. For example, a human subject with knee OA may receive one, two, or three injections of about 2, 3, 4, 5, 6, 7, 8, 9, 10 ml or more per knee. For other joints, the administered volume can be adjusted based on the size on the joint.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

EXPERIMENTAL DATA

Example 1

In Vitro Evaluations

Multiple in vitro studies were performed to test the hypothesis that the observed rhGDF-5 precipitation in HA would negatively impact the bioactivity/potency of rhGDF-5.

Combinations of rhGDF-5 in different diluents with and without HA were compared for the extent of rhGDF-5 precipitation. rhGDF-5 was suspended in 10 mM HCl pH 2.0, which was then combined with (1) phosphate-buffered saline (PBS), (2) 1mM HCl, (3) 0.9% saline, and (4) trehalose plus excipients (F-18) to form separate formulations. Each of these formulations was subsequently mixed with HA (Orthovisc®) with a final concentration of rhGDF-5 of 0.5 mg/mL in 0.5% HA. HA control formulations were made by combining the respective diluents (phosphate-buffered saline (PBS), 1 mM HCl, 0.9% saline and Trehalose plus excipients) with HA in the absence of rhGDF-5 to a final concentration of 0.5% HA, and HA-free controls were made by further diluting the intermediate rGDF-5 formulations in diluent to a final concentration of 0.5 mg/mL rhGDF-5. The pH of the resultant formulations was determined and they were visually assessed for rhGDF-5 precipitation.

Precipitation of rhGDF-5 was observed in the presence of HA formulations and PBS alone. Different aliquots of the same formulations demonstrated minimal variation. The extent of rhGDF-5 precipitation correlated with rhGDF-5 concentration.

As detailed below in Table 1, relative to 0.5% HA control formulations, the combination of rhGDF-5 at 0.5 mg/ml with HA resulted in cloudy precipitants for all formulations. Select formulations were further evaluated, including rhGDF in PBS or PBS+HA and rhGDF-5 in F18 (trehalose+excipients) or F18+HA. rhGDF-5 in 1 mM HCl (pH 3.0) alone was included as a positive control as the protein is known to remain fully soluble at this pH.

TABLE 1

Visual assessment for rhGDF-5 precipitation and pH

| Group | Formulation | pH | rhGDF-5 Solubility |
|---|---|---|---|
| 1 | PBS | 6.8 | No, Cloudy |
| 2 | PBS + HA | 6.6 | No, Cloudy |
| 3 | F18 | 4.9 | No, Particulates |

TABLE 1-continued

Visual assessment for rhGDF-5 precipitation and pH

| Group | Formulation | pH | rhGDF-5 Solubility |
|---|---|---|---|
| 4 | F18 + HA | 4.9 | No, Slightly Cloudy |
| 5 | HCl (1 mM) | 2.7 | Yes, Clear |
| 6 | HCl + HA | 3.9 | No, Cloudy + Aggregates |
| 7 | Saline (0.9%) | 2.9 | Yes, Clear |
| 8 | Saline + HA | 3.9 | No, Cloudy + Aggregates |

*Formulations prepared using rhGDF-5 Batch in 10 mM HCl, pH = 2.0
***PBS pH = 7.1, F18 pH = 5.4, 1 mM HCl pH = 3.0, 0.9% Saline pH = 5.1, HA pH = 5.7

Formulation Homogeneity

Figure 3:
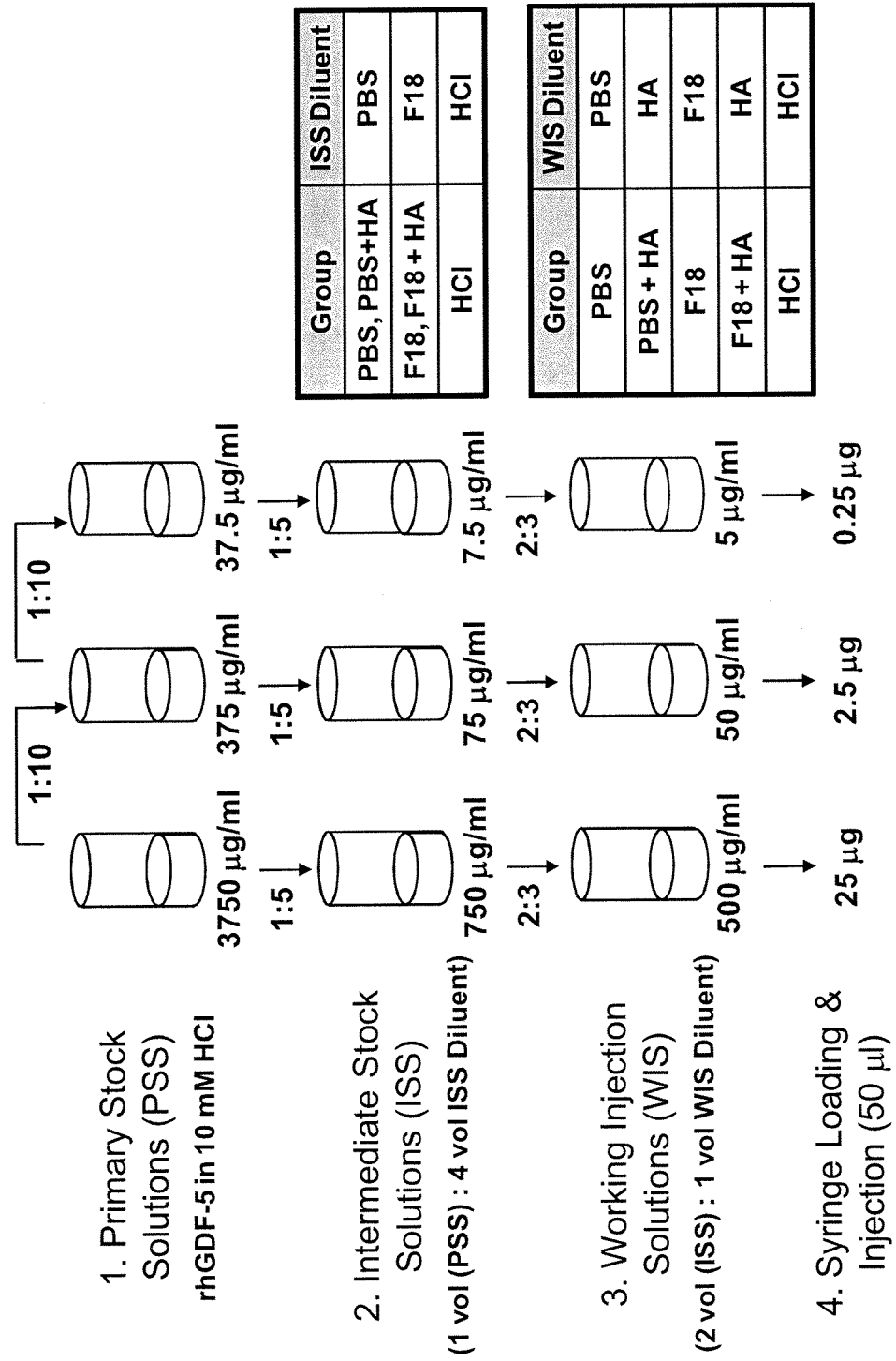
FIG. 3 illustrates the method of preparation of the test solutions for ELISA from a stock solution of rhGDF-5 in 10 mM HCl. Final concentrations of rhGDF-5 were made at 0.5, 0.05 and 0.005 mg/mL in the respective diluents.

FIG. 3 details the method used for preparation of test solutions for ELISA from a stock solution of rhGDF-5 in 10 mM HCl. Batches of ~2 mL were prepared with final concentrations of rhGDF-5 at 0.5, 0.05 and 0.005 mg/mL in the respective diluents. rhGDF-5 concentrations were determined in 50 microliter aliquots using standard ELISA techniques to assess homogeneity (at time t=0) and stability (at time t=0, 24, and 120 hrs) of the resulting formulation.

Figure 4:
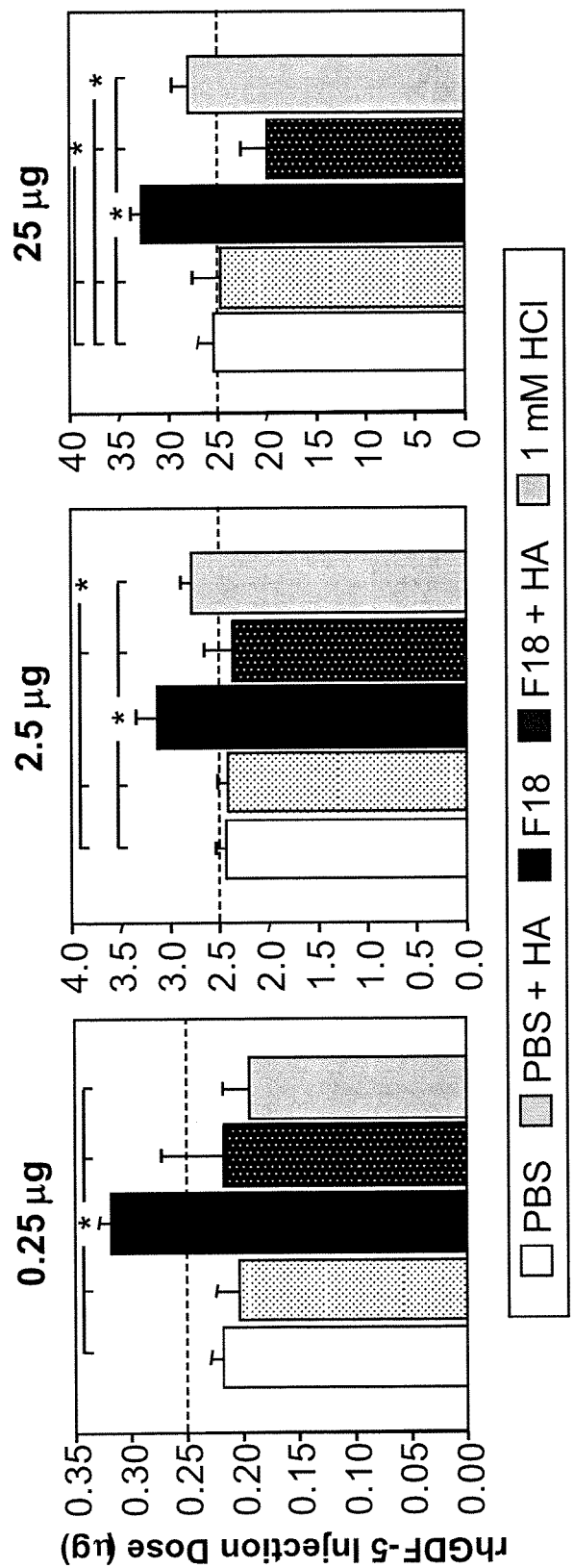
FIG. 4 depicts standard ELISA techniques to assess homogeneity (at time t=0) and stability (at time t=0, 24, and 120 hrs) of batches of ~2 mL preparations with varying rhGDF-5 concentrations in 50 microliter aliquots.

FIG. 4 shows the correlation to the theoretical solution concentration that was injected, even though rhGDF-5 was observed to have precipitated in the presence of HA formulations and PBS alone. Additionally, the concentrations demonstrated minimal variation within the different aliquots of the same formulation. Surprisingly, homogeneity of precipitate rhGDF-5 in the HA formulations was observed without regard to the relative viscosity of the HA solution.

Formulation Stability

Figure 5:
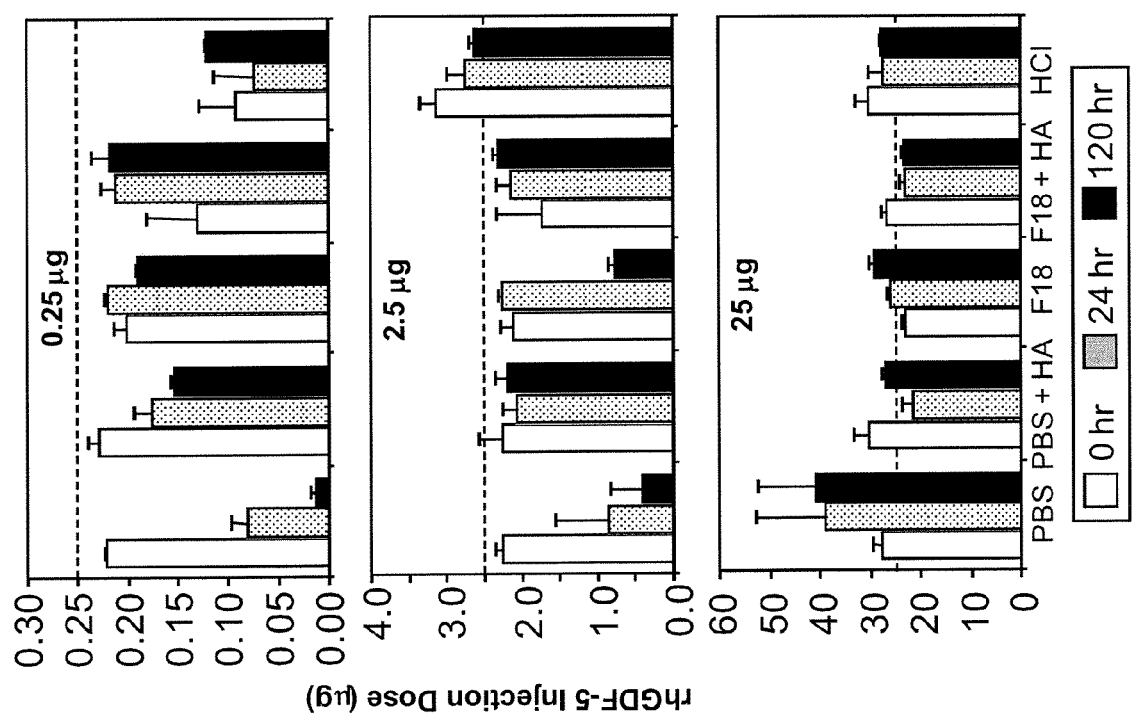
FIG. 5 shows a graphical representation of formulations prepared and stored at 4° C. prior to ELISA testing to measure stability over time.

The stabilization of the formulations was also tested by ELISA. Formulations were prepared at time t=0 and stored at 4° C. prior to ELISA testing. FIG. 5 shows that stability of rhGDF-5 by HA in an aqueous solution near neutral pH (~6.6) was observed, even over short time frames. Relative to the formulation of rhGDF-5 in PBS alone, rhGDF-5 in PBS+HA demonstrated less variation in solution concentration and improved stability over time, as rhGDF-5 concentrations were comparable to the theoretical solution concentration even out to 120 hours at all doses/concentrations evaluated. Therefore, it is believed that HA imparts stability to the protein especially at low concentrations (e.g., less than 2.5 ug) because the ELISA data (see FIG. 5) show that after 24 and 120 hours, more protein is recovered than when the protein is in PBS alone. This implies that the presence of HA is important for preserving the activity of the growth factor. That is, to the extent that the protein is biologically inactive in its solid, precipitated form, it becomes biologically active after injection into a patient. Similar results were observed for rhGDF-5 formulated in trehalose+excipients (F18) with and without HA, as solution concentrations appeared to remain stable over the time frame evaluated. The pH of the F18 and F18+HA solutions was ~4.9. As expected, the HCl only control group (pH=2.7) was stable over time at each of the concentrations evaluated.

Bioactivity

Figure 6:
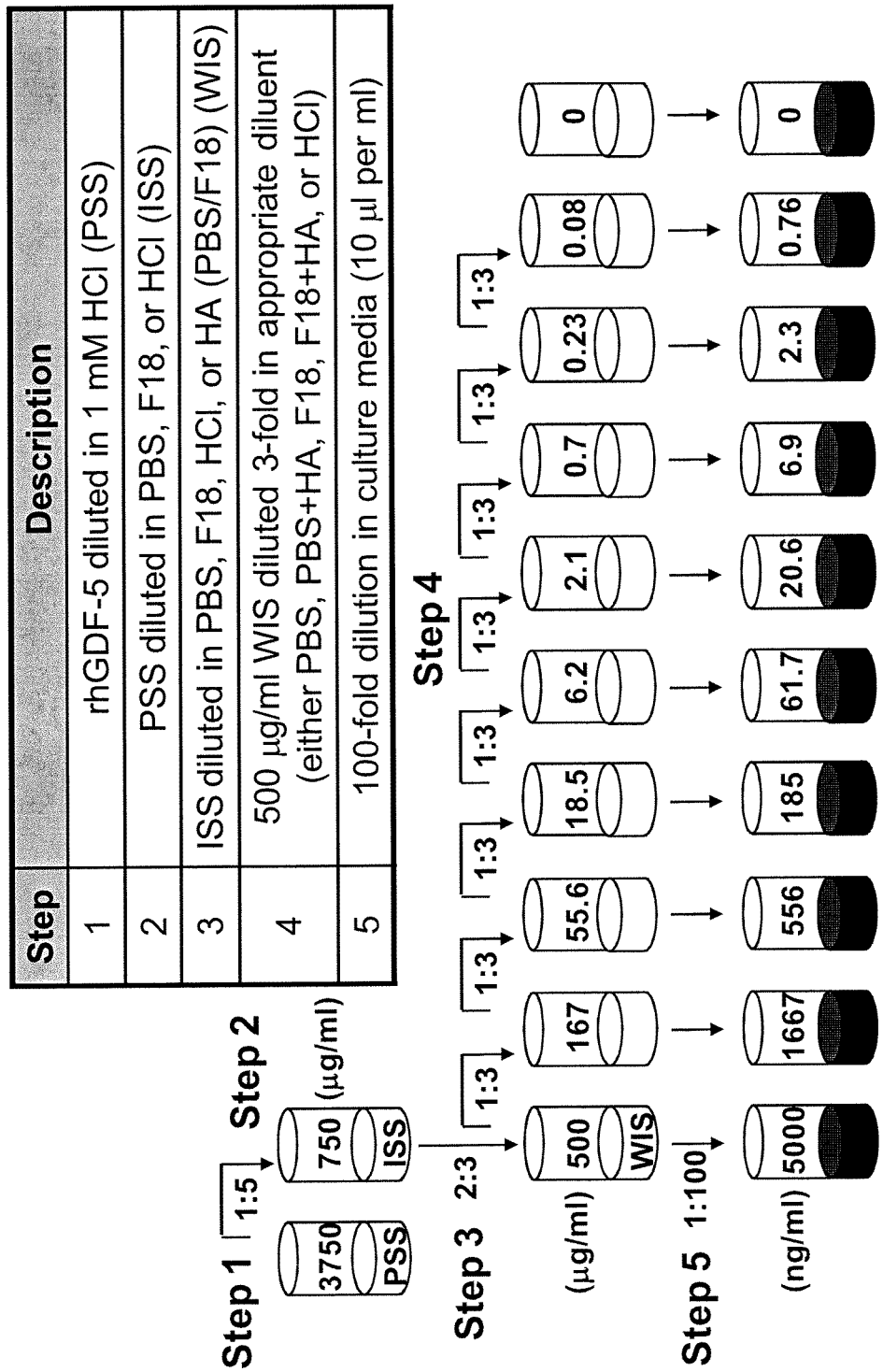
FIG. 6 illustrates the protocol for the bioactivity test in a well-established chondrogenic bioassay.

Bioactivity of the formulations was also assessed in a well-established chondrogenic bioassay assessing dose-dependent sulfated glycosaminoglycan (sGAG) concentration produced by pellet cultures of juvenile bovine chondrocytes, which is shown in FIG. 6. The method involved pelleting ~250,000 chondrocytes and culturing them in presence of a serum-free media combined with rhGDF-5 formulations in HA or a positive control formulation of rhGDF-5 in 1.0 mM HCl. Cultures were then maintained for 14 days with media changes containing fresh rhGDF-5 formulations every 3-4 days. At the experimental termination, cultures were digested in papain and assayed for sGAG accumulation using a well established DMMB (dimethylmethylene blue) absorbance assay. Test articles were prepared as detailed in the schematic of FIG. 6 (the concentrations denote the working concentration of rhGDF-5).

Figure 7:
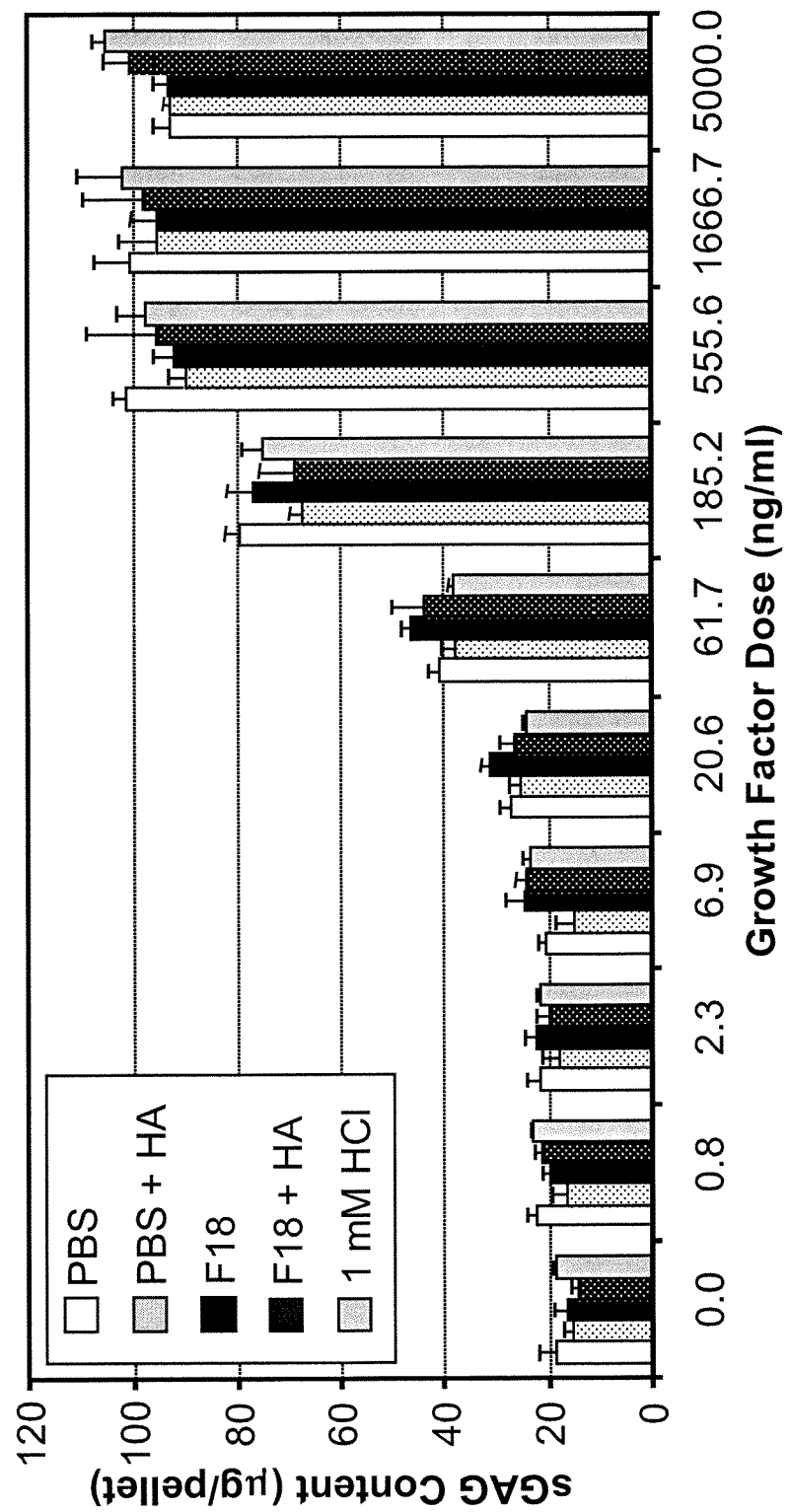
FIG. 7 illustrates graphical results of the chondrogenic assay to measure bioactivity.

FIG. 7 summarizes the results from the chondrogenic assay. It was observed that the rhGDF-5 formulations containing HA demonstrated a comparable dose-dependent bioactivity to "naked" rhGDF-5 protein in 1 mM HCl despite the observation that protein was precipitated in the HA formulations. This demonstrates that the suspension of rhGDF-5 in HA is active after injection into a patient.

Example 2

In Vivo Evaluations

An in vivo animal study was conducted to evaluate the intra-articular activity of rhGDF-5 formulated in HA. Intra-articular injections of rhGDF-5/HA formulations, shown in Table 2, were evaluated in normal/healthy rat knees to assess tolerance to the injection and intra-articular bioactive response. Semi-weekly injections were performed for a total of 3 weeks (6 injections total) of rhGDF-5 formulated in PBS+0.5° A HA (Orthovisc®), and a total of 7 animals per group were evaluated. The study design is detailed in Table 2.

TABLE 2

Intra-articular injection of rhGDF-5/HA formulations

| Group Name | Injection Solution (ug/ml) | Dose Solution (ug/ml) | Total Dose (ug/ml) |
|---|---|---|---|
| rhGDF-5 Low | 5 | 0.25 | 1.5 |
| rhGDF-5 Middle | 50 | 2.5 | 15 |
| rhGDF-5 High | 500 | 25 | 150 |

Based on the study design to evaluate a two-decade dilution series of rhGDF-5, and HA only control was not included in this screening study. The results of the study demonstrated the injection series was well-tolerated in all study groups as no lameness or inflammation was observed. An rhGDF-5 dose-dependent response was observed in the study groups, as the high dose group (25 micrograms per injection) demonstrated the most pronounced intra-articular effects (see FIG. 8A) as opposed to the untreated contralateral joint (see FIG. 8B). Mild synovitis and chondrogenesis was observed in the marginal zones of the highest dose (25 micrograms per injection) study group. In vivo and intra-articular bioactivity was observed regardless of precipitation of the rhGDF-5 in the HA formulations.

Terminology

A therapeutically effective amount or effective amount can be administered of the composition to achieve a pharmacological effect. The term "therapeutically effective amount" includes, for example, a prophylactically effective amount. An "effective amount" is an amount effective to achieve a desired pharmacologic effect or therapeutic improvement without undue adverse side effects. For example, an effective amount refers to an amount that increases operativity, or increases weight bearing load, or decreases pain, or increases growth in the bone and cartilage of one or more joints, or reduces joint distortion, pain, swelling, or stiffness. The effective amount of an agent will be selected by those skilled in the art depending on the particular patient and the disease level. It is understood that "an effect amount" or "a therapeutically effective amount" can vary from subject to subject, due to variation in metabolism of therapeutic agents such as s and/or prokinetic agents, age, weight, general condition of the subject, the condition being treated, the severity of the condition being treated, and the judgment of the prescribing physician.

"Treat" or "treatment" refers to any treatment of a disorder or disease associated with bone or cartilage disorder, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder. Thus, as used herein, the term "treat" is used synonymously with the term "prevent."

By "co-administered" is meant simultaneous administration in the same formulation or in two different formulations that are combined into one formulation for adminstration. In one embodiment, the HA and the BMP are co-administered via delivery in the same formulation.

The term "subject" as used herein refers to an animal, preferably a mammal and more preferably human who can benefit from the compositions and methods of the present invention. There is no limitation on the type of animal that could benefit from the present methods. A subject regardless of whether a human or non-human animal may be referred to as an individual, subject, animal, host or recipient. The methods of the present invention have applications in human medicine, veterinary medicine as well as in general, domestic or wild animal husbandry. Preferably, the candidate subject is a mammal such as a human or laboratory test animal such as a mouse, rat, rabbit, guinea pig, hamster or avian species such as a poultry bird.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for treating a joint condition, comprising:
combining a solution of hyaluronic acid (HA) with a bone morphogenetic protein (BMP) to form a mixture in which the BMP is precipitated and dispersed at a concentration in the range of about 5 µg/ml to 90 µg/ml in the solution of HA, the mixture having a pH in the range of about 3 to 8; and
injecting the mixture into a subject to treat the joint condition, the BMP being capable of becoming solubilized and biologically active within the subject after injection.

2. The method of claim 1, wherein the BMP is a growth and differentiation (GDF) protein.

3. The method of claim 1, wherein the BMP is in a liquid state prior to combining with the solution of HA.

4. The method of claim 1, wherein the BMP is in a lyophilized state prior to combining with the solution of HA.

5. The method of claim 1, wherein the mixture has a pH in the range of about 4 to 7.5.

6. The method of claim 1, wherein the HA has a molecular weight of at least about 500 kDa.

7. The method of claim 1, wherein the HA is at a concentration in the range of About 5 mg/ml to 60 mg/ml.

* * * * *